(12) United States Patent
Fischer

(10) Patent No.: US 6,346,108 B1
(45) Date of Patent: Feb. 12, 2002

(54) PROBE FOR COAGULATION OF BIOLOGICAL TISSUE

(75) Inventor: Klaus Fischer, Nagold (DE)

(73) Assignee: Erbe Electromedizin GmbH (DE)

( * ) Notice: Subject to any disclaimer, the term of this patent is extended or adjusted under 35 U.S.C. 154(b) by 0 days.

(21) Appl. No.: 09/425,700

(22) Filed: Oct. 22, 1999

(30) Foreign Application Priority Data

Oct. 22, 1998 (DE) .......................................... 198 48 784

(51) Int. Cl.⁷ .............................................. A61B 18/18
(52) U.S. Cl. ............................ 606/49; 606/40; 606/41
(58) Field of Search ............................ 606/49, 45, 46; 219/147, 74

(56) References Cited

U.S. PATENT DOCUMENTS 5,614,117 A * 3/1997 Krobath ..................... 219/147
5,720,745 A * 2/1998 Farin et al. ..................... 606/49
6,039,736 A * 3/2000 Platt ............................. 606/49
6,210,410 B1 * 4/2001 Farin et al. ..................... 606/49

FOREIGN PATENT DOCUMENTS

DE          41 39 029 A1    6/1993
DE          197 11 673 A1   10/1998

* cited by examiner

*Primary Examiner*—Michael Peffley
*Assistant Examiner*—Pete Vrettakos
(74) *Attorney, Agent, or Firm*—St. Onge Steward Johnston & Reens LLC

(57) ABSTRACT

A probe for use in the coagulation of biological tissue by plasma discharge comprises a protective device with a mask made of an insulating material. The mask is so constructed and attachable to the probe that parts of the biological tissue that are vulnerable or other parts that likewise should not be coagulated can be shielded by the masking region.

8 Claims, 2 Drawing Sheets

PROBE FOR COAGULATION OF BIOLOGICAL TISSUE

FIELD OF THE INVENTION

The present invention relates to a probe for the coagulation of biological tissue.

DESCRIPTION OF THE PRIOR ART

German patent DE 41 39 029 A1 discloses a probe for the coagulation of biological tissue in which an ionizable inert gas, in particular argon, is delivered by gas-supply means to a gas outflow opening formed at a distal end of the probe, coaxially or in a side wall. In the interior of the probe electrode devices are provided to conduct a coagulation current from a high-frequency source into the gas and through the gas into the biological tissue, which is devitalized by the current or by the heat produced in the ionized gas.

One of the problems associated with the known arrangement is that the plasma current, i.e. the region of ionized gas within the overall gas current, cannot be aimed entirely accurately, and hence the site in the biological tissue through which current flows cannot be precisely delimited. This problem becomes considerable when an operation is to be carried out in a very confined region such as a narrow cavity in the body. One example is the use of plasma coagulation in cases of nasal concha hyperplasia. In such confined spaces there is a risk that the argon plasma beam will unintentionally be applied to healthy tissue or to vulnerable structures such as nerves.

The object of the present invention is to provide a probe of the kind described above that overcomes or substantially mitigates the aforementioned problems and that facilitates its manipulation with increased safety.

SUMMARY OF THE INVENTION

According to the present invention there is provided a probe for the coagulation of biological tissue, comprising a probe body defining a gas outflow opening; a gas-supply means to supply an ionizable inert gas or noble gas to the outflow opening; an electrode to conduct a coagulation current from an HF source into the gas and through the latter into the biological tissue; and a protective device comprising a mask which is made of an insulating material and which is so constructed and attachable to the body of the probe that regions of the biological tissue that should not be coagulated can be shielded by the mask.

The shielding that can be achieved by both the direct contact between the mask and the part of the tissue to be protected and also by the insulating material of which the mask is made increases the distance the arc would have to travel to reach the protected tissue. In this way, the arc is directed only to the parts of the tissue closer to the opening or within a shorter distance of travel.

Preferably, the probe body is of an elongated, tubular construction and defines the outflow opening in a side wall thereof. In this case the mask is preferably positioned on the side of the probe opposite the gas outflow opening, so that the gas stream emerging from the side of the probe produces a plasma beam that is only aimed in substantially this direction and that does not, on account of special electrical conditions, for example caused by a particularly low resistance of certain parts of the tissue, suddenly migrate backward, toward the side of the probe opposite the outflow opening.

Preferably also, at least the mask of the protective device is made from a flexibly deformable material. In addition, the mask is advantageously from an elastically deformable material. This makes it possible for the protective device or the mask to be brought into contact with the part of the tissue that is not to be coagulated with no fear of mechanical injury. Given an appropriate construction of the protective device, namely such that it projects beyond the distal end of the probe, it can be ensured that the protective device as a whole can be used to prevent mechanical injury to tissue by the probe.

Preferably also, the protective device is detachably fastened to the body of the probe. The device can then be sterilized before each re-use or be constructed as a disposable component manufactured by injection molding.

Preferably also, the mask defines a spade- or spoon-shape with an uninterrupted surface. Advantageously the mask projects forward beyond the end region of the probe as well as outward on both sides, to ensure a secure and simple masking of parts of the tissue that should not be coagulated.

Preferably also, the mask is made of a transparent material in order that a user can see clearly the area below the mask, which further simplifies manipulation of the probe.

An embodiment of the invention will now be described by way of example with reference to the accompanying drawings.

DESCRIPTION OF THE PREFERRED EMBODIMENTS

Figure 1:
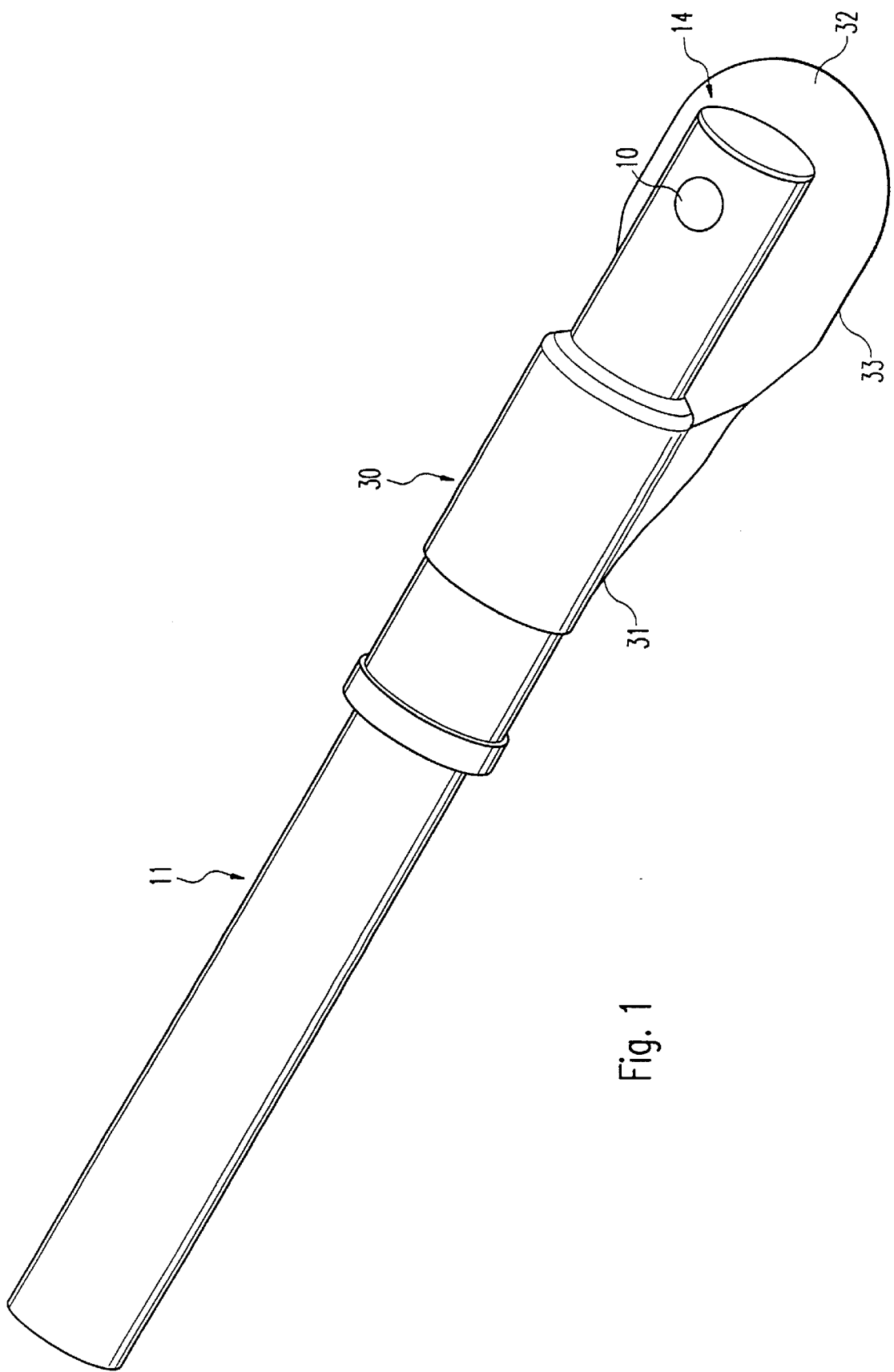
FIG. 1 is a perspective view of the exterior of a probe according to the invention.

In the following description, the same reference numerals are used for identical parts or parts with identical actions.

An apparatus for the coagulation of biological tissue shown in FIG. 1, comprises a probe 11 with an elongated body at a distal end 14 of which is defined an outflow opening 10 that is positioned radially relative to the long direction of the probe 11. The distal end 14 of the probe 11 is made of a ceramic material or protected by a coating of ceramic material, so that even at relatively high temperatures, such as are produced by a plasma, any plastics material of the probe 11 is not damaged.

At the end of the probe 11 a protective device 30 is provided, which is made of a flexible, soft plastics material and is firmly seated on the probe 11 by way of an annular mounting section 31. From the mounting section 31 a mask 32 extends forward, projecting beyond the distal end 14 of the probe 11. An edge 33 of the mask 32, which is of extremely smooth construction in order to avoid injuries, extends beyond the longitudinal end of the probe 11 and also at the sides, as shown in FIG. 1. The region delimited by the mask 32 is substantially spade- or spoon-shaped and the mask 32 itself is preferably made from a transparent material.

Figure 2:
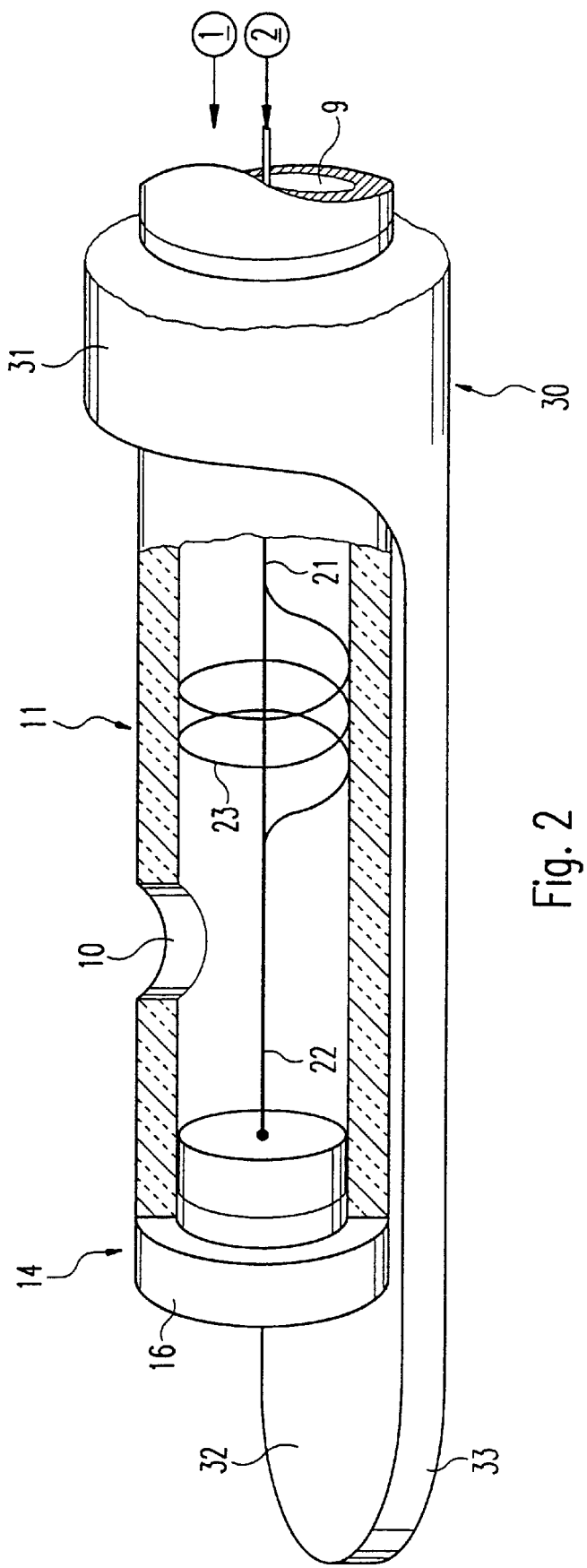
FIG. 2 is a perspective view from the side, in partial cross-section, of the probe shown in FIG. 1.

As shown in FIG. 2 a noble gas, in particular argon, is conducted from a gas source 1 through a gas-supply conduit 9 in the probe 11, the gas-supply conduit being closed at its distal end 14 by an end-piece 16.

In the interior of the probe 11 or of the gas-supply conduit 9 there is a current conductor 21, which is attached to an HF source 2 so as to supply a coagulation current. In the end region of the probe 11 the current conductor 21 is held in the middle by a holder 23, in such a way that an electrode 22 (the terminal section of the current conductor 21) is positioned in the center of the gas-supply conduit 9 and extends past the outflow opening 10.

The probe 11 is guided toward tissue to be coagulated in such a way that when the tissue has been reached, the outflow opening 10 is substantially aimed at the part that is to be coagulated. During operation, argon gas is sent from the gas source 1 into the gas-supply conduit 9, emerges from the outflow opening 10 and strikes the tissue region to be coagulated. Hence, between the tissue region and the electrode 22 there is an argon atmosphere. Now when the HF source 2, one contact of which is coupled to the probe 11 and the other to the tissue to be coagulated, provides a coagulation current, a plasma is formed between the electrode 22 and the tissue, in a process known per se. During an operation in a confined body cavity it can happen that after the tissue surface opposite the outflow opening 10 has dried out, the arc could migrate to the back side of the probe 11, i.e. to the side diametrically opposite the outflow opening 10, and there destroy sensitive tissue, or tissue that ought not to be treated becomes coagulated or is necrotized. However, because the protective device 30 is provided, the situation is altered as follows. First, the path the discharge would have to take from the outflow opening 10 to the tissue next to and below the mask 32 is made considerably longer than the path to the tissue regions directly opposite the outflow opening 10. As a result of this increase in travel distance, with a suitable setting of the HF source 2 it can be ensured that if the plasma does migrate in this direction, with a corresponding lengthening of the discharge path, it will be extinguished. Furthermore, the mask 32 can be placed in direct contact with those parts that must be protected. Because of this direct apposition, the surface to be protected is isolated from the argon atmosphere so that no discharge can take place there.

The protective device 30, in addition to this electrical protective function, also has a purely mechanical protective function, because owing to its shape and dimensions, the mask 32 prevents the distal section 14 from making direct contact with the tissue to be treated, at least in the end region opposite the outflow opening 10.

What is claimed is:

1. A probe for the coagulation of biological tissue, comprising a probe body extending along a longitudinal axis and defining a gas outflow opening which is spaced radially from the longitudinal axis;

a gas-supply means to supply an ionizable inert gas to the outflow opening;

an electrode to conduct a coagulation current from an HF source into the gas and through the latter into the biological tissue;

a protective device comprising a mask which is made of an insulating material and which is so constructed and attachable to the probe body that regions of the biological tissue that should not be coagulated can be shielded by the mask while the gas outflow opening is unshielded; and wherein the protective device is detachably fastened to the body of the probe.

2. A probe as claimed in claim 1, wherein the mask defines a spoon-shape with an uninterrupted surface.

3. A probe as claimed in claim 1, wherein the mask is made of a transparent material.

4. A probe as claimed in claim 1, wherein the mask defines a spade-shape with an uninterrupted surface.

5. A probe for the coagualtion of biological tissue, comprising a probe body extending along a longitudinal axis and defining a gas outflow opening which is spaced radially from the longitudinal axis;

a gas-supply means to supply an ionizable noble gas to the outflow opening;

an electrode to conduct a coagulation current from an HF source into the gas and through the latter into the biological tissue;

a protective device comprising a mask which is made of an insulating material and which is so constructed and attachable to the probe body that regions of the biological tissue that should not be coagulated can be shielded by the mask while the gas outflow opening is unshielded; and wherein the protective device is detachably fastened to the body of the probe.

6. A probe as claimed in claim 5, wherein the mask defines a spoon-shape with an uninterrupted surface.

7. A probe as claimed in claim 5, wherein the mask is made of a transparent material.

8. A probe as claimed in claim 5, wherein the mask defines a spade-shape with an uninterrupted surface.

* * * * *